United States Patent [19]

Tidwell et al.

[11] 4,397,863
[45] Aug. 9, 1983

[54] INHIBITION OF RESPIRATORY SYNCYTIAL VIRUS-INDUCED CELL FUSION BY AMIDINO COMPOUNDS

[75] Inventors: Richard R. Tidwell; Edward J. Dubovi; Joachim D. Geratz, all of Chapel Hill, N.C.

[73] Assignee: Research Triangle Institute, Research Triangle Park, N.C.

[21] Appl. No.: 366,652

[22] Filed: Apr. 8, 1982

Related U.S. Application Data

[62] Division of Ser. No. 181,341, Aug. 26, 1980, Pat. No. 4,324,794.

[51] Int. Cl.$^3$ .................. A61K 31/40; A61K 31/415; A61K 31/155
[52] U.S. Cl. ........................... 424/274; 424/273 B; 424/326
[58] Field of Search ........................................ 424/274

[56] References Cited

PUBLICATIONS hemical Abstracts 91:188592a (1979).
hemical Abstracts 95:330u (1981).
hemical Abstracts 96:48178y (1982(.
idwell et al., J. Med. Chem., vol. 21, No. 7, 1978, pp. 613-623.

*Primary Examiner*—Jerome D. Goldberg
*Attorney, Agent, or Firm*—Cushman, Darby & Cushman

[57] ABSTRACT

A number of aromatic mono- and bis-amidines are capable of blocking cell fusion induced by Respiratory Syncytial (RS) virus. Suitable amidino compounds include those selected from the group consisting of 1-4-di(4-amidinophenoxy)-2-butanol; bis(5-amidino-2-benzimidazolyl)methane; 1,2-bis(5-amidino-2-benzimidazolyl)ethane; 5-amidino-indole; 5-amidinobenzimidazole, 5-amidino-1-methylindole and 5-amidino-1-(4-amidinobenzyl)indole. The most powerful of the compounds, bis(5-amidino-2-benzimidazolyl)methane (BABIM), is able to achieve complete suppression of syncytium formation at a concentration of 1 $\mu$M. Inhibition occurs in RS virus-infected Hep-2 cells as well as CV-1 cells. BABIM also causes a significant retardation of RS virus penetration, but does not interfere with adsorption. Addition of the amidines after the penetration of RS virus does not affect single cycle yields. The compounds may be used in the prophylactic control of RS virus in man.

5 Claims, No Drawings

INHIBITION OF RESPIRATORY SYNCYTIAL VIRUS-INDUCED CELL FUSION BY AMIDINO COMPOUNDS

The invention described relates to a method for inhibiting Respiratory Syncytial Virus-induced cell fusion and was made in the course of work under a grant or award from the Department of Health, Education and Welfare.

This is a division of application Ser. No. 181,341 filed Aug. 26, 1980 and now U.S. Pat. No. 4,324,794.

BACKGROUND OF THE INVENTION

In man, respiratory syncytial (RS) virus is responsible for the majority of respiratory illnesses suffered by children during the first five years of life. Symptoms are those of coryza, bronchitis and bronchopneumonia and may last from days to several weeks. While recovery is the usual outcome, morbidity is often quite significant and may necessitate aggressive symptomatic clinical treatment including mechanical respiratory assistance. Epidemiologic studies also suggest the possibility of a causal relationship between overt RS virus infection and the development of asthma later in childhood. Despite recognition of the clinical and economic importance of RS virus infections, neither preventive nor suppressive treatment is available. Attempts to provide active vaccination have met with failure, and as yet no effective anti-viral drug has been found. This state of affairs has led to the present invention providing for new avenues to the control of the virus.

RS virus has been grouped as a member of the genus pneumovirus within the family of paramyxoviridae. Like the other two genera in this family, i.e., the paramyxoviruses and the morbilliviruses, it is characterized by a helical arrangement of the RNA-containing nucleocapsid, by the possession of an outer envelope bearing numerous projections ("spikes") and by its ability to produce cell fusion in tissue cultures. For at least three members of the genus paramyxovirus, i.e., Sendai virus, 6/94 virus, and Newcastle disease virus, a trypsin-like proteolytic activity is a necessary factor in achieving full expression of the biologic properties of the virions (Scheid and Choppin, Identification of biological activities of paramyxovirus glycoproteins. Activation of cell fusion, hemolysis, and infectivity by proteolytic cleavage of an inactive precursor protein of Sendai virus. Virology 57, 475–490 (1974); Waters et al., The potential role of phagocytically active cells in establishing chronic parainfluenza 1 virus infections in human brain J. Neur. Sci. 25, 491–498 (1975): Nagai and Klenk, Activation of precursors to both glycoproteins of Newcastle disease virus by proteolytic cleavage. Virology 77, 125–134 (1977). It has been clearly demonstrated that the action of the putative enzyme involves the post-translational cleavage of a virion glycoprotein which is changed from an inactive precursor into an active fusion (F) protein. The F protein plays a central role in the fusion of virions with cell membranes, in the formation of the characteristic syncytia in cell cultures and also in the virus-dependent lysis of red cells (Scheid and Choppin, supra. Biologically, the factor controls infectivity and virulence of the viruses and the severity of the cytopathic effect.

The general similarities in both the morphologic and cytopathogenic characteristics of these three viruses and RS virus suggested to us the possibility that a protease might also participate in the replication of the latter agents. If so, suppression of the cleavage event could be expected to interfere with the cytotoxic activities and with the replication of the viruses (Korant, Proteolytic events in viral replication. In *Molecular Basis of Biological Degradative Processes.* (R. D. Berlin, H. Herrmann, I. H. Lepow, and J. M. Tanzer, eds.), pp. 171–224, Academic Press, New York, 1978). To this end, RS virus was cultured in the presence of a series of reversible inhibitors of arginine-directed (i.e., trypsin-like) esteroprotease. The investigation led to the discovery of seven compounds which strongly blocked RS virus-induced cell fusion. It should be noted, that inhibitory potency per se does not allow any judgment as to the mode of action of the compounds. Inhibition of post-translational hydrolytic cleavage of virus proteins, may play a role, but may not be the only, or even the major factor involved.

Despite recognition of the clinical and economic importance of RS virus infections, neither effective preventive nor suppressive treatment is available. Attempts to provide active vaccination have met with failure, and as yet no effective antiviral drug has been found. This state of affairs has led to the present invention providing for new avenues to the control of the virus.

Accordingly, it is a primary object of the present invention to provide a method for inhibiting Respiratory Syncytial Virus-Induced Cell Fusion.

This and other objects of the present invention will be more apparent from the discussion below.

SUMMARY OF THE INVENTION

Cell fusion induced by Respiratory Syncytial Virus is inhibited according to the present invention by several aromatic mono- and bis-amidines.

Among the aromatic amidino compounds which have been found to be inhibitively effective against RS virus are those selected from the group consisting of 1-4-di(4-amidinophenoxy)-2-butanol; bis(5-amidino-2-benzimidiazolyl)methane; 1,2-bis(5-amidino-2-benzimidazolyl)ethane; 5-amidinoindole, 5-amidinobenzimidazole, 5-amidino-1-methylindole and 5-amidino-1-(4-amidinobenzyl)indole. These compounds are active when contacted with cells susceptible to RS virus induced fusion in an inhibitory effective amount. Suitable dosages of the specific amidino compounds range from about 1.0 to 10.0 $\mu$M.

While the group most seriously hit by RS virus is children ranging from six months to two years of age, there is a substantial problem in older age groups, particularly those confined in extended care facilities and retirement homes. It is therefore also contemplated according to the present invention that the effective amidino compounds be administered to individuals in an effective amount to provide prophylactic treatment and thereby avoid epidemics of RS virus. The mode of administration can be oral, by inhalation or parenteral. Since the effect of the compounds appears to be a surface activity, there is no apparent need to penetrate the cell in order to be effective in preventing or inhibiting fusion of cells.

The inhibitory activity of the amidines is not dependent on a single type of host cell, but occurs with any of several cell lines which are susceptible to the characteristic cytopathic effect of RS virus. The suppressive effect is virus specific, however, and does not extend to cell fusion induced by P-3 virus or the MP mutant of herpes simplex type 1. Though the compounds do not interfere with virus adsorption or with replication per se, they do retard or block penetration, and reduce the yield from multiple growth cycles of RS virus. As a possible explanation for these findings and not wishing to be limited thereto, it is believed that the inhibitors impede the fusion of the virions with the cell membrane if added to the monolayers together with the virus, and that they block fusion from within if added after the adsorption and penetration period. It also follows that under the latter condition any newly formed and released virions would be hindered from infecting adjacent cells and that spread under a multiple cycle growth pattern would therefore be restricted. This was well demonstrated morphologically by the focal limitation of the cytopathic effect at low multiplicities of infection by RS virus.

The aromatic mono-amidines and aromatic bis-amidines which may be employed according to the present invention are compounds 5, 7, 8, 9, 11, 12 and 13 set forth in Table 1.

TABLE 1

| Compound No. | Name | Amidine Structure |
|---|---|---|
| 1 | Benzamidine | Am—⌬ |
| 2 | Pentamidine | Am—⌬—O(CH$_2$)$_5$O—⌬—Am |
| 3 | 1-(4-Amidinophenoxy-6-phenoxyhexane | Am—⌬—O(CH$_2$)$_6$—O—⌬ |
| 4 | 1-(4-Amidinophenoxy)-8-phenoxyoctane | Am—⌬—O(CH$_2$)$_8$—O—⌬ |
| 5 | 1,4-Di(4-amidinophenoxy)-2-butanol | Am—⌬—O(CH$_2$)$_2$CH(OH)CH$_2$O—⌬—Am |
| 6 | α,α′-Bis(4-amidino-2-iodophenoxy)-m-xylene | Am—⌬(I)—OCH$_2$—⌬—CH$_2$O—⌬(I)—Am |
| 7 | Bis(5-amidino-2-benzimidazolyl)methane | Am—[benzimidazole]—CH$_2$—[benzimidazole]—Am |
| 8 | 1,2-Bis(5-amidino-2-benzimidazolyl)ethane | Am—[benzimidazole]—(CH$_2$)$_2$—[benzimidazole]—Am |
| 9 | 5-Amidinoindole | Am—[indole] |
| 10 | 5-Amidinobenzofuran | Am—[benzofuran] |

| Compound No. | Name | Amidine Structure |
|---|---|---|
| 11 | 5-Amidinobenzimidazole | 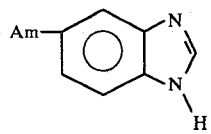 |
| 12 | 5-Amidino-1-methylindole | 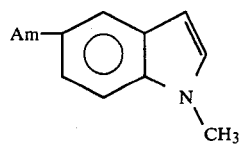 |
| 13 | 5-Amidino-1-(4-amidino-benzyl)indole | 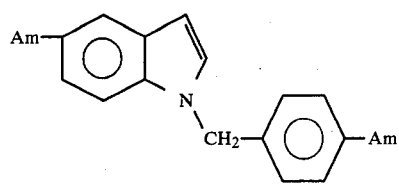 |

$^a$Am = $-\text{C} \begin{smallmatrix} \text{NH} \\ \text{NH}_2 \end{smallmatrix}$

DETAILED DESCRIPTION OF THE INVENTION

The influence of the aforementioned amidino compounds (Table 1) on RS virus was revealed by their effect on various aspects of virus growth in cell cultures. For an inhibitor to be judged acceptable, cell toxicity had to be excluded as the basis of the observed anti-RS virus activity. The specificity of the compounds was demonstrated by their inability to interfere with the growth of other viruses studied.

The Examples below are offered to more fully describe the present invention, but are not to be construed as limiting the scope thereof.

MATERIALS AND METHODS

Viruses and Cell Cultures

Hep-2, HeLa, and CV-1 cells were propagated in Eagle minimal essential medium (MEM) supplemented with 10% fetal calf serum (FCS). In experiments involving protease inhibitors, Hep-2 cells were used between passages 371 and 377.

An $A_2$ strain of RS virus was grown in Hep-2 cells. Stock cultures of virus were prepared by inoculating suspensions of Hep-2 cells. Following virus adsorption, the infected cells were seeded in 250 ml plastic culture flasks containing MEM plus 10% FCS. When viral cytopathic effects were maximal (72–96 hr.) the flasks were frozen at $-70°$ C. Typical lysates contained $10^7$–$10^8$ TCID$_{50/ml}$.

Parainfluenza type 3 (P-3) was obtained from the Research Resources Branch, NIAID (cat #V-323-002-020). Stocks of P-3 were produced in HeLa cells by infecting confluent monolayers and harvesting culture fluid after 48 hrs. Stock cultures containing $10^8$TCID$_{50/ml}$ were stored at $-70°$ C.

A polykaryocyte-forming mutant (MP) of herpes simplex type 1 (HSV-1) was also employed.

All virus stocks and cell lines were determined to be free of mycoplasma contamination by a modification of the fluorochrome technique of Chen. (In situ determination of mycoplasma contamination in cell cultures by fluorescent Hoeshst 33258 stain. Experimental Cell Research, 104, 255–262 (1977)).

Viral Titrations

Virus yields were quantitated by calculating 50 percent end points according to the method of Reed and Muench (A simple method for estimating fifty percent end-points. Am. J. Hyg. 27, 493–497 (1938)). Briefly, 0.05 ml of virus diluted in MEM plus 10% FCS was added to micro-titer plates. This was followed by the addition of 40,000–60,000 Hep-2 cells in a volume of 0.05 ml. Plates were incubated at 36° C. for 5–7 days. Six or eight wells were used for each dilution. Standard error analysis was done according to the method of Pizzi (Sampling variation of the fifty percent endpoint determined by the Reed-Muench (Behrens) method. Human Biol. 22, 151–180 (1950)).

Amidino Compounds

Thirteen competitive, reversible inhibitors of trypsin-like enzymes selected for this study are listed with their structures in Table 1. The first compound, benzamidine, represents the prototype of inhibitors with an amidine nature, and since the time it was first described by Mares-Guia and Shaw (Studies on the active center of trypsin. The binding of amidines and guanidines as models of the substrate side chain. J. Biol. Chem. 140, 1579–1585 (1965)) it has served as a key building block for other, more potent agents, such as compounds no. 2–6. Pentamidine, which is active against a wide variety of trypsin-like enzymes, is generally an order of magnitude more effective than benzamidine (Geratz, Specific low-molecular weight inhibitors of trypsin. Their structure-activity relationships and possible clinical uses. In *Pulmonary Emphysema and Proteolysis.* (C. Mittman, ed.) pp. 325–340. Academic Press, New York, 1972;

Geratz et al., Diamidino- α,ω-diphenoxylalkanes. Structure-activity relationships for the inhibition of thrombin, pancreatic kallikrein, and trypsin. J. Med. Chem., 16, 970–975, 1973; Geratz and Tidwell, The development of competive reversible thrombin inhibitors. In *Chemistry and Biology of Thrombin. (R. L. Lundblad, J. W. Fenton, II, and K. G. Mann, eds.), pp.* 179–196, Ann Arbor Science, 1977). Compounds 3 and 4 are similar in structure to pentamidine, but they possess only a single amidino group and are endowed with increased hydrophobicity as a consequence of the lengthened hydrocarbon chain. Compound 5 represents a strong inhibitor of the plasminogen activator urokinase with a $K_i$ value of $3.2 \times 10^{-6}$ M (Geratz and Cheng, The inhibition of urokinase by aromatic diamidines. Thromb. Diath. Haemorrh. 33, 230–243, 1975), while no. 6 is one of the most powerful inhibitors of pancreatic kallikrein with a $K_i$ value of $3.1 \times 10^{-8}$ M (Geratz et al., Novel bis(benzamidino) compounds with an aromatic central link. Inhibitors of thrombin, pancreatic kallikrein, trypsin, and complement. J. Med. Chem., 19, 634–639, 1976). In no. 7 we selected the amidino compound with the greatest antitrypsin activity so far reported ($K_i = 1.8 \times 10^{-8}$ M) (Tidwell et al., Diarylamidine derivatives with one or both of the aryl moieties consisting of an indole or indole-like ring. Inhibitors of arginine-specific esteroproteases. J. Med. Chem. 21, 613–623, 1978), and in no. 8 its closest homolog was included, differing from the parent compound only by bearing an additional hydrocarbon in the central molecular chain. Compounds 9–11 are isosteric amidino-substituted heterocycles of small molecular size which can be accommodated solely in the specificity pockets of their target enzymes and achieve much tighter binding than benzamidine (Geratz et al., Amidino-substituted aromatic heterocycles as probes of the specificity pocket of trypsin-like proteases. Arch. Biochem. Biophys., 197, 551–560, 1979). Compounds 12 and 13, finally, are derivatives of 5-amidinoindole bearing a substitution on the indole nitrogen (Geratz et al., 1979, ibid.).

Compounds 3 and 4 were synthesized in our laboratory and have not been previously reported. The two novel derivatives were prepared and purified according to a general synthetic procedure for the synthesis of unsymmetrical α,ω-diphenoxyalkane derivatives (Geratz et al., Diamidino-α,ω-diphenoxyalkanes. Structure-activity relationships for the inhibition of thrombin, pancreatic kallikrein, and trypsin. J. Med. Chem., 16, 970–975, 1973). The melting points (M.P.) and elemental analyses of compounds 3 and 4 are as follows:

of infection in 0.2 ml was adsorbed for 2 hrs. at 36° C. Following this period, the wells were rinsed twice with 1 ml of MEM and received either inhibitor-containing or control media consisting of MEM with 2% FCS and 1% methyl sulfoxide (DMSO). Cell viability was measured by trypan blue exclusion and cytopathology were scored at 24 and 40 hr. following addition of the inhibitors. Total virus yields from cultures harvested at 40 hr. post infection were determined following one freeze-thaw cycle at −70° C.

The effect of the inhibitors on viral penetration (Table 6) was determined as follows: RS virus grown in the presence or absence of compound 7 was serially diluted in MEM containing 2% FCS and 1% DMSO with or without 50 μM of compound 7. Aliquots of 0.05 ml were added to wells of microtiter plates containing monolayers of Hep-2 cells. Virus was adsorbed for 2 hrs. at 36° C. RS virus and then antiserum diluted 1:8 in MEM, was added to the appropriate wells. Following an additional one hour of incubation, all monolayers were then rinsed and overlayed with 0.1 ml of MEM plus 5% FCS. Titers were determined at 5–7 days.

RESULTS

The Effect of Amidino Compounds on Cell Viability

In order to separate the cytotoxic properties of the inhibitors from specific antiviral activities, Hep-2 cell cultures incubated with each of the compounds for 24 and 40 hrs. were examined for viability by the trypan blue exclusion test. Table 2 lists as toxic those concentrations of inhibitors which resulted in the uptake of dye by more than 10% of the cells harvested. Among the 13 compounds investigated, only no. 2 (pentamidine) and no. 1 (benzamidine) had previously been tested for their cytotoxic potential. The former reduced cell growth rates at concentrations of 5–40 μM (Goldberg et al., Plasminogen activators of transformed and normal cells. In *Proteases and Biological Control* (E. Reich, D. B. Rifkin, and E. Shaw, eds.), pp. 857–868, Cold Spring Harbor Laboratory, 1975) and the latter at concentrations greater than 500 μM (Taylor and Lembach, Reversible inhibition of cell multiplication in vitro by inhibitors of arginine esteroproteases. Biochim. Biophys. Acta 329, 58–71, 1973). Those concentrations of the two agents are in the same general range in which clear-cut toxicity was observed in the present assay system (Table 2). From the data in Table 2 it can also be seen that only one other compound, no. 6, was as toxic as pentamidine. Five inhibitors, nos. 3–5, 12 and 13 were intermediate in their cytotoxicity, and an additional five, nos. 7–11

| Compound 3: | $C_{19}H_{24}N_2O_2 \cdot HCl$ | Molecular Weight = 348.88 | | |
|---|---|---|---|---|
| M.P. = 290–292° C. | Analysis: | | C | H | N |
| | | Calculated | 65.42 | 7.22 | 8.03 |
| | | Found | 65.32 | 7.02 | 8.29 |
| Compound 4: | $C_{21}H_{28}N_2O_2 \cdot HCl \cdot 0.5H_2$ | Molecular Weight = 385.93 | | |
| M.P. = 100–102° C. | Analysis: | | C | H | N |
| | | Calculated | 65.35 | 7.83 | 7.25 |
| | | Found | 65.58 | 8.07 | 7.34 |

The melting points were determined on a Thomas-Hoover capillary melting point apparatus and are uncorrected.

Inhibitor Studies

Hep-2 cells or CV-1 cells were seeded in well trays to contain approximately $10^6$ cells per well at 72 hrs. RS virus or P-3 virus added at various input multiplicities possessed the same or even less toxic activity than benzamidine. It was also established that Hep-2 cells are not unique in their response to amidines. An identical pattern of toxicity was observed with a representative group of the compounds (nos. 2, 3, 6 and 7) when tested on three other cell lines, i.e., A549 (human lung), CV-1

(monkey kidney), and BHK-21 (hamster kidney) (data not shown).

TABLE 2

Cytotoxic Effect of Amidines on Hep-2 Cell Viability

| Compound Number | Concentration (μM) | | | | | | | |
|---|---|---|---|---|---|---|---|---|
| | 5000 | 1000 | 500 | 100 | 50 | 10 | 1.0 | 0.1 |
| 1 | T[1] | nd[2] | T | nd | C[3] | nd | nd | nd |
| 2 | T | nd | T | nd | T | T | C | C |
| 3 | nd | T | nd | T | nd | C | nd | nd |
| 4 | nd | T | nd | T | nd | C | nd | nd |
| 5 | nd | T | nd | T | nd | C | C | C |
| 6 | nd | T | nd | T | nd | T | C | C |
| 7 | T | nd | C | nd | C | C | C | C |
| 8 | nd | T | nd | C | nd | C | C | C |
| 9 | nd | T | nd | C | nd | C | C | C |
| 10 | nd | T | nd | C | nd | C | nd | nd |
| 11 | nd | nd | nd | C | nd | C | C | C |
| 12 | nd | nd | nd | T | nd | C | C | C |
| 13 | nd | nd | nd | T | nd | C | C | C |

[1] Toxic
[2] not done
[3] Control viability (no cytotoxicity)

Influence of Amidino Compounds on the Cytopathic Effects of RS Virus and P-3 Virus The role of proteolytic modification of viral glycoproteins in the activation of cell fusing activity is well established for paramyxoviruses. With this in mind, the presence or absence of syncytium formation was initially used to score the impact of the protease inhibitors on the replication of RS virus and P-3 virus. The amidino compounds were added to the Hep-2 cell cultures after viral adsorption and penetration (2 hour post infection). Therefore, any inhibitor-related modification of the cytopathic effects must have had its origin in the alteration of the later stages of virus replication. All compounds were tested in serial dilutions and syncytium formation was evaluated by inspection of infected cultures at low microscopic power. In the case of P-3 virus, none of the compounds exhibited any effect on the cytopathic effect and inhibitor-treated cultures were morphologically identical to the control. This was in striking contrast to the RS virus-infected cultures in which seven compounds (nos. 5, 7–9, 11, 12 and 13) suppressed the appearance of the characteristic syncytia (Table 3). One of the amidines (no. 7) was active at concentrations at least 100 times lower than their cytotoxic level. The structural specificity of the inhibition is shown by the ability of compound 7 to inhibit syncytium formation at a concentration as low as 1.0 μM and by the lower activity of compound 8 which is a structural homolog of compound 7.

Morphologically, the changes in the RS virus cytopathic effect produced by the inhibitors were easily recognized. Uninfected control cultures showed some single rounded cells on the monolayer while virus-infected Hep-2 cells (multiplicities of infection 1-2, 40 hrs. post infection) had formed syncytia of varying sizes. Treatment of RS virus-infected cells with a 1.0 μM concentration of compound 7 resulted in abolition of fusion to the extent that infected monolayers did not appear different than uninfected controls.

The modification of the cytopathic effect at the level of individual foci of infection (multiplicity of infection 0.01, 96 hrs. post infection) was also striking. The characteristic pattern of RS virus cpe in Hep-2 cells involves the fusion of cells adjacent to the initially infected cell. This results in the progressive enlargement of the syncytium until the edges of the syncytium begin to contract. This contraction results in a thinning of the monolayer around the syncytium or the development of an area devoid of cells. In the presence of the inhibitors, no fusion of cells was seen at the focus of infection. Instead, the infected cells aggregate, forming clusters of non-fused cells with no apparent thinning of the adjacent monolayer.

This reduction of cytopathology was even more obvious in RS virus infected CV-1 cells examined at 8 days post infection. It was observed that in untreated infected cultures over 50% of the monolayer was destroyed during the multiple cycles of RS virus growth. However, treatment of similarly infected CV-1 cells with a 50 μM concentration of compound 7 resulted in the preservation of the monolayer with individual foci of infection appearing to be inhibited in their spread to uninfected areas of the culture. This inhibition of the RS virus cytopathic effect was not due to toxicity of compound 7 over a prolonged period of cell exposure. CV-1 cells maintained in a medium containing a 50 μM concentration of compound 7 for 6 days produced normal yields of P-3 and HSV-1 when challenged on day 6. It should also be noted that compound 7 had no effect on the ability of the MP mutant of HSV-1 to fuse CV-1 cells.

TABLE 3

Effect of Amidines on RS Virus Cytopathology

| Compound Number | Concentration (μM) | | | | | | |
|---|---|---|---|---|---|---|---|
| | 1000 | 500 | 100 | 50 | 10 | 1.0 | 0.1 |
| 1 | nd[1] | T[2] | nd | S[3] | nd | nd | nd |
| 2 | nd | T | nd | T | T | S | S |
| 3 | T | nd | T | nd | S | nd | nd |
| 4 | T | nd | T | nd | S | nd | nd |
| 5 | T | nd | T | nd | NS[4] | S | S |
| 6 | T | nd | T | nd | T | S | S |
| 7 | nd | NS | nd | NS | NS | NS | S |
| 8 | T | nd | NS | NS | NS | S | S |
| 9 | T | nd | NS | NS | NS | S | S |
| 10 | T | nd | S | nd | S | nd | nd |
| 11 | nd | nd | NS | nd | S | S | nd |
| 12 | nd | nd | nd | nd | NS | NS | NS |
| 13 | nd | nd | nd | nd | NS | S | S |

[1] not done
[2] Toxic
[3] Syncytia Present
[4] Absence of Characteristic Syncytial Development Effect of Amidines on The Yields of RS Virus and P-3 Virus With paramyxoviruses, the coordinate expression of infectivity and the ability to induce cell fusion strongly suggests that these two activities are controlled by the same viral protein. The relationship between infectivity and cell fusion has not been established for RS virus. The availablity of the fusion inhibitors permitted us to examine this question for RS virus. With a large inoculum (multiplicites of infection 1-2) added prior to the addition of the inhibitors, the suppression of virus-induced cell fusion had no detrimental effect on essentially single-cycle yields of RS virus as shown in Table 4. Lower than control values were obtained only in those instances where toxicity had been demonstrated (Table 2). In fact, the yield data seem to duplicate the findings with the trypan blue exclusion test indicating that the outcome of either assay reflects the integrity and competence of the inhibitor-treated cells. In addition, the amidino compounds did not alter the yields of P-3 virus at high multiplicities of infection.

TABLE 4

Effect of Amidines on Single Cycle Yields of RS Virus

| Compound Number | Concentrations (μM) | | | | |
|---|---|---|---|---|---|
| | 1000 | 500 | 100 | 50 | 10 |
| 1 | nd[a] | 2.8 × 10^4[c] | nd | 1.1 × 10^7 | nd |
| 2 | nd | T[b] | nd | 6.3 × 10^4 | nd |
| 3 | T | nd | T | nd | 3.5 × 10^7 |
| 4 | T | nd | T | nd | 3.5 × 10^7 |
| 5 | T | nd | 5.0 × 10^5 | nd | 0.5 × 10^7 |
| 6 | T | nd | T | nd | 6.3 × 10^6 |
| 7 | nd | 2.0 × 10^7 | nd | 6.3 × 10^7 | nd |
| 8 | T | nd | 7.9 × 10^7 | nd | 6.3 × 10^7 |
| 9 | T | nd | 6.3 × 10^7 | nd | 2.9 × 10^7 |
| 10 | T | nd | 6.3 × 10^7 | nd | 1.1 × 10^7 |
| 11 | nd | nd | 8.7 × 10^7 | nd | nd |
| 12 | nd | nd | nd | nd | nd |
| 13 | nd | nd | nd | nd | nd |

[a] not done
[b] Toxic
[c] RS virus titers in TCID$_{50}$/ml
Control RS virus titers 1–5 × 10^7

At low multiplicities of infection, however, the findings were different from those just discussed. For these experiments, Hep-2 cells were infected with either RS virus or P-3 virus at multiplicities of infection of 0.1, 0.01, or 0.001. Following a 2 hour absorption period, the cultures received medium with or without a 50 μM concentration of compound 7. The monolayers were harvested after multiple cycles of replication and the yields were determined in inhibitor-free microtiter assays. As shown in Table 5, considerably less RC virus was obtained from the inhibitor-treated monolayers than from the controls. This confirmed the impressions from the earlier visual observations that presence of inhibitor greatly reduced the spreading of RS virus. Even at high multiplicities of infection, pretreatment of Hep-2 cells with a 50 μM concentration of compound 7 resulted in a 1–2 log reduction of RS yields. The results in Table 5 also reveal that the inhibitor produced a slight, but consistent decrease in the yield of P-3 virus.

TABLE 5

Multiple Cycle Yields of RS Virus and P-3 Virus

| Virus | moi | Yields (TCID$_{50}$/ml) | |
|---|---|---|---|
| | | Control | Treated[d] |
| RS | 0.1[a] | 5.0 × 10^7 | 6.3 × 10^6 |
| RS | 0.01[b] | 3.2 × 10^7 | 1.2 × 10^5 |
| RS | 0.001[b] | 2.8 × 10^6 | 1.1 × 10^4 |
| P-3 | 0.1[c] | 3.5 × 10^8 | 7.9 × 10^7 |
| P-3 | 0.01[c] | 7.9 × 10^7 | 4.6 × 10^7 |
| P-3 | 0.001[a] | 2.0 × 10^8 | 6.3 × 10^7 |

[a] Harvested 72 hr post infection
[b] Harvested 120 hr post infection
[c] Harvested 48 hr post infection
[d] 50 μM compound 7

Effect of Compound 7 on Adsorption and Penetration of RS Virus

In the following experiments, the ability of compound 7 to interfere with adsorption and/or penetration of RS virus was studied since restrictions in these areas of the infection cycle could explain the data in Table 5. Interference with viral penetration can be assessed by determining whether adsorbed virus is accessible to virus specific antiserum. This approach was used employing a modification of the standard TCID$_{50}$ assay of RS virus.

Briefly, RS virus was grown on Hep-2 cell monolayers in the absence or presence of a 50 μM concentration of compound 7. After 40 hours, the supernatant was harvested and serially diluted in MEM with or without 50 μM of compound 7. A 0.05 ml aliquot of each dilution was added to eight preformed Hep-2 cell monolayers in microtiter plates. Following a 2 hour adsorption period at 36° C., 0.05 ml of either MEM or MEM containing a 1:8 dilution of RS virus antiserum was added to the wells and the incubation continued for an additional hour. The monolayers were then rinsed and overlayed with 0.1 ml of MEM plus 5% FCS. Titers were determined at 5–7 days.

From the data in Table 6, it is evident that attachment of the virus was not blocked by the inhibitor because the final titers in group 2 versus 4 and group 6 versus 8 were identical. Since the inocula in these groups were all removed at the same time, any interference with adsorption should have expressed itself in a reduction in titer in the inhibitor-containing assays as compared to the inhibitor-free controls. A comparison of groups 3 versus 4 and groups 6 versus 7 shows that the addition of antiserum to the inhibtor-free virus cultures did not significantly affect the final titer, i.e., most of the adsorbed virus had already penetrated the cells by 2 hours and was beyond neutralization by antibodies. However, if inhibitor was present during the adsorption period and the cultures were then exposed to antiserum, a significant reduction in titer was observed as compared to the inhibitor-free, antiserum-treated controls (group 1 versus 3; group 5 versus 7). These findings indicate that a delay in RS virus penetration occurred under the influence of inhibitor so that the virions remained susceptible to the inactivating effect of the antiserum.

It should also be noted that the RS virus which had replicated in the presence of inhibitor (RSI series in Table 6) did not behave differently from the control (C series) which had been grown in the absence of inhibitor. With virus from both sources, penetration was delayed to a similar degree and, as already pointed out, there was not interference with adsorption. This result argues against the idea that inhibition by amidines of post-translational proteolytic modification of newly synthesized viral proteins was responsible for the delay in viral penetration. There was recorded, however, throughout all control groups a higher titer than in the RSI series. Since only released virus and not total virus was harvested, no significance can be attached to the differences between the RSI series and the control series.

TABLE 6

Effect of Fusion Inhibitor on the Penetration of RS Virus

| Titer # | Titer Conditions | TCID$_{50}$ (Log 10) | Standard Error |
|---|---|---|---|
| 1 | RSI +I +A | 4.11 | .33 |
| 2 | RSI +I +A | 5.97 | .26 |
| 3 | RSI −I +A | 5.50 | .30 |
| 4 | RSI −I +A | 5.97 | .26 |
| 5 | C +I +A | 5.59 | .31 |
| 6 | C +I −A | 6.92 | .37 |
| 7 | C −I +A | 6.73 | .24 |
| 8 | C −I +A | 6.97 | .26 |

RSI = RS virus grown in presence of cpd 7 (50 μM)
C = RS virus grown in absence of cpd 7
+I = Presence of cpd 7 during adsorption of RS virus
−I = Absence of cpd 7 during adsorption of RS virus
+A = Addition of anti-RS serum 2 hrs. after addition of virus to Hep-2 cell monolayers
−A = No anti-RS serum treatment The invention having thus described, it will be apparent that various departures can be made therefrom without departing from the scope or spirit thereof.

We claim:

1. A method for the treatment of respiratory syncytial virus-induced cell fusion which comprises administering to a host in need of said treatment to an effective amount of an aromatic amidine compound selected from the group consisting of 5-amidinoindole and 5-amidino-1-methylindole.

2. The method of claim 1 wherein said amidine is administered in an effective amount ranging from about 1.0 to 10.0 M.

3. The method of claim 1 or 2 wherein said amidine is 5-amidino-1-methylindole.

4. The method of claim 1 wherein the mode of administration is oral.

5. The method of claim 1 wherein the host is a human.

* * * * *